United States Patent [19]

Griggs

[11] Patent Number: 4,571,289

[45] Date of Patent: Feb. 18, 1986

[54] PHOTOCHEMICAL PROCESS FOR THE PRODUCTION OF ALKYLENE GLYCOLS

[75] Inventor: Colin G. Griggs, Ashford, England

[73] Assignee: The British Petroleum Company, p.l.c., London, England

[21] Appl. No.: 681,006

[22] Filed: Dec. 13, 1984

[30] Foreign Application Priority Data

Dec. 30, 1983 [GB] United Kingdom ................. 8334611

[51] Int. Cl.[4] .............................................. B01J 19/12
[52] U.S. Cl. .................................................... 204/157.9
[58] Field of Search .................................... 204/158 R

[56] References Cited

FOREIGN PATENT DOCUMENTS

| 14657 | 7/1964 | Japan | 204/158 R |
| 154520 | 9/1983 | Japan | 204/158 R |

*Primary Examiner*—Howard S. Williams
*Attorney, Agent, or Firm*—Brooks, Haidt, Haffner & Delahunty

[57] ABSTRACT

Alkylene glycols are prepared by reaction of an alcohol with formaldehyde and an organic peroxide having a formula $R-O-O-R^1$ where R and $R^1$ are independently either alkyl or aralkyl groups containing 3 to 12 carbon atoms. The reaction is carried out in the presence of electromagnetic radiation which is able to decompose the organic peroxide. The alcohol used in this process is either methanol, a secondary alcohol or a mixture thereof.

10 Claims, No Drawings

PHOTOCHEMICAL PROCESS FOR THE PRODUCTION OF ALKYLENE GLYCOLS

The present invention relates to a process for the production of alkylene glycols.

Alkylene glycols are industrially important chemicals. Thus the simplest alkylene glycol, ethylene glycol, is a very large tonnage industrial chemical which finds direct use in automotive coolant and antifreeze solutions, as a heat-transfer agent in refrigeration, and as an ingredient of deicing fluids for airport runways. Its uses as a chemical intermediate include its incorporation as an essential constituent in polyester fibers, films and bottle resins. It is also used as a solvent in for example lacquers, printing inks and adhesives.

In recent years, emphasis has shifted away from traditional methods of manufacturing ethylene glycol towards routes which utilise synthesis gas (gaseous mixtures comprising carbon monoxide and hydrogen), largely because synthesis gas can be derived not only from petroleum but also from such raw materials as natural gas and coal, and potentially from oil shale and tar sands. Thus, according to U.S. Pat. Nos. 2,316,564; 2,153,064; 2,152,852; 2,285,448; and 2,331,094, ethylene glycol can be produced by reacting formaldehyde with carbon monoxide and water at high pressures (over 300 bars) in the presence of an acid catalyst to produce hydroxyacetic (glycollic) acid, reacting the acid so-produced with methanol to form the methyl ester and thereafter converting the methyl ester to ethylene glycol by catalytic hydrogenation. Another process, disclosed in U.S. Pat. Nos. 4,115,428 and 4,115,433, describes the production of ethylene glycol by reacting methanol and carbon monoxide at high pressures using a rhodium catalyst.

Even more recently, GB patent applications publication Nos. 2083037 and 2083038, U.S. Pat. No. 4,393,252 and European patent publication Nos. 71457 and 71458 relating to the production of ethylene glycol by reacting methanol, formaldehyde and an organic peroxide have appeared. GB-A-2083038 discloses a process for producing ethylene glycol by reacting methanol, an organic peroxide, and formaldehyde in the presence of water (suitably from about 0.5 to about 35 weight per cent), said organic peroxide having the formular R—O—O—$R^1$ wherein R and $R^1$ each is an alkyl or aralkyl group containing 3 to 12 carbon atoms, wherein no more than about 6 per cent of organic peroxide, based on the total weight of methanol, organic peroxide, formaldehyde and water present, is utilised in the initial reaction mixture. GB-A-2083037 describes a similar process in which a basic material is added to the reactants in an amount sufficient to reduce the hydrogen ions that are being formed in the reaction without unduly reducing the ethylene glycol production due to by-product formation. In Examples 13 and 14 of GB-A-2083037 the monomeric aqueous formaldehyde was produced from paraformaldehyde by adding a small amount of hydrogen chloride to depolymerise the paraformaldehyde to aqueous monomeric formaldehyde and thereafter the formaldehyde solution was neutralised by the addition of a small amount of sodium bicarbonate. U.S. Pat. No. 4,393,252 discloses subject matter similar to that of GB-A-2083037. EP-A-71457 discloses the improvement wherein the formaldehyde and the organic peroxide are added portionwise at intervals throughout the reaction period. Finally EP-A-71458 discloses the improvement wherein the amount of the peroxide used is greater than 6 and up to 25 weight percent and the amounts of water used is from 0.5 to 36 weight percent, and the amount of the peroxide and water used are dependent on each other so that either the amount of the peroxide used is greater than 6 up to 12 weight percent and the amount of water used is from 0.5 to 35 weight percent, or the amount of the peroxide used is greater than 12 up to 15 weight percent and the amount of water used is from 0.5 to 25 weight percent, or the amount of the peroxide used is greater than 15 up to 20 weight percent and the amount of water used is from 0.5 to 15 weight percent, or the amount of the peroxide used is greater than 20 up to 25 weight percent and the amount of water used is from 0.5 to 10 weight percent, the above weight percentages being based on the total weight of the methanol, organic peroxide, formaldehyde and water present in the reaction mixture.

Our copending European patent application No. 11066 describes a process for the production of ethylene glycol which process comprises reacting at elevated temperature methanol, a polymeric source of formaldehyde and an organic peroxide having the formula R—O—O—$R^1$ wherein R and $R^1$ are independently either alkyl or aralkyl groups containing from 3 to 12 carbon atoms.

We have now found that organic peroxides can be decomposed by electromagnetic radiation of suitable wavelength in the presence of methanol or secondary alcohols and formaldehyde to produce the corresponding alkylene glycols, for example methanol can be converted to ethylene glycol. The process can thus be operated at ambient temperature and can produce glycols in high selectivities. Moreover, the alcohol resulting from cleavage of the peroxide can be recovered at high selectivities also.

Accordingly, the present invention provides a process for the production of an alkylene glycol from formaldehyde and either methanol or a secondary alcohol which process comprises reacting the formaldehyde with the methanol or secondary alcohol in the presence of an organic peroxide having the formula R—O—O—$R^1$ wherein R and $R^1$ are independently either alkyl or aralkyl groups containing from 3 to 12 carbon atoms characterised in that the reaction is carried out in the presence of electromagnetic radiation capable of decomposing the organic peroxide.

Methanol, a secondary alcohol or a mixture of such alcohols may be used as reactants. The secondary alcohol may be any monofunctional or polyfunctional secondary alcohol but is suitably a monofunctional secondary alcohol. Preferred monofunctional secondary alcohols are those having between 3 and 20 carbon atoms and include, for example, propan-2-ol, butan -2-ol, pentan-2-ol, pentan-3-ol, 2-methylbutan-2-ol, hexan-2-ol, 2 methylpentan-2-ol, 2,3-dimethylbutan-2-ol, cyclohexanol and cycloheptanol. In addition to the alcohol groups, the secondary alcohol may be substituted with other groups such as halide, cyanide and the like.

The organic peroxide having the formula R—O—O—$R^1$ wherein R and $R^1$ are independently either alkyl or aralkyl groups containing from 3 to 12 carbon atoms may suitably be di-tertiary-butyl peroxide, di-cumyl peroxide, tertiary-butyl cumyl peroxide or tertiary-butyl ethyl benzyl peroxide. Preferably the peroxide is either di-cumyl peroxide or ditertiary-butyl peroxide.

The electromagnetic radiation employed must be of a wavelength and intensity capable of decomposing the organic peroxide. Suitably the radiation may have a wavelength in the range from 250 to 400 nanometers. Preferably the radiation is ultra-violet radiation. The source of electromagnetic radiation can be a lamp, for example a mercury vapour lamp or the like.

The reaction may be carried out in the presence of formaldehyde or a polymeric source of formaldehyde. Thus formaldehyde may be added as formalin, which is an aqueous solution of formaldehyde. Alternatively, formaldehyde may be generated by depolymerisation of a formaldehyde polymer, for example paraformaldehyde or trioxane. In a further alternative a polymeric source of formaldehyde may be added directly. Suitable polymeric sources of formaldehyde include paraformaldehyde, otherwise known as paraform, trioxane and tetraoxane, of which paraformaldehyde is preferred. Paraformaldehyde is a solid mixture of linear poly(oxymthylene glycols) of relatively short chain length and may be represented by the formula $Ho(CH_2O)_nH$, wherein n is 8–100. Commercially available forms of paraformaldehyde generally have an average molecular weight of about 600 and may contain up to about 9 wt % water and a maximum acidity as formic acid of 0.03 wt %. Such commercially available forms may be used in the process of the present invention without further purification. Alternatively, the commercially available forms may be further purified before use in the process. If desired, higher molecular weight, i.e. n greater than 100, suitably in the range from 100 to 500, forms of polyoxymethylene glycols of the formula $HO(CH_2O)_nH$ may be employed. Trioxane, which may also be used in the process of the present invention is the cyclic symmetrical trimer of formaldehyde and is also a solid. Trioxane is also commercially available. Tetraoxane, which is a cyclic tetramer of formaldehyde, is a solid.

The process may be operated in the presence of water, using reactants which have not been dried, optionally with additional water. Alternatively the process of the invention may be operated under substantially anhydrous conditions, i.e. at a water content of less than 0.5% by weight, preferably less than 0.25% by weight, based on the total weight of the reactant mixture. It may be necessary when operating under substantially anhydrous conditionsto use at least partially dried reactants.

As hereinbefore mentioned, the process may be operated at ambient temperature, or if desired elevated tempeatures may be employed.

The process may be operated at autogenous pressure, that is the pressure generated in a closed reactor at the particular reaction temperature, though pressures above and below autogenous may be used if so desired. Generally, the reaction time for a batch operation may suitably be in the range from 0.25 to 4 hours., depending upon the relative concentrations of the reactants and the intensity of the electromagnetic radiation.

The process may be operated batchwise, semi-continuously or continuously, preferably continuously.

The organic peroxide may be added to the methanol or secondary alcohol in a single addition or in a number of separate additions at intervals throughout the reaction.

The product mixture may be purified using conventional techniques, such as distillation or solvent extraction, to recover the alkylene glycol. Besides the glycol there will also be formed, as a by-product of the cleavage of the organic peroxide, the corresponding alcohol, for example using ditertiary butyl peroxide as the organic peroxide there will also be formed tertiary butanol, which is itself a valuable product.

The process of the invention will now be illustrated by reference to the following Examples.

EXAMPLES 1–3

Into a 400 ml capacity immersion well photoreactor was added known amounts of paraformaldehyde, or aqueous formalin di-tertiary-butyl peroxide (DTBP) and methanol; the reactor was then closed to the air. The contents of the immersion reactor were then irradiated at 21° C. for 4h with a 400W medium pressure mercury source. After 4h the irradiation was stopped, the reactor opened and its contents analysed.

The compositions of the initial reaction mixtures and analyses of the reaction products are given in the accompanying Table.

TABLE

| Example | $CH_3OH$ | $CH_2O$ | $(CH_2O)_n$ | $H_2O$ | DTBP | $\frac{\text{mmol EG}}{\text{mmol DTBP}}$ | EG* yield (%) | TBA + select (%) |
|---|---|---|---|---|---|---|---|---|
| 1 | 80 | 8.2 | — | 11.8 | 2.0 | 3.1 | 154 | 94 |
| 2 | 93.2 | — | 4.5 | — | 2.3 | 2.8 | 142 | 95 |
| 3 | 92.8 | — | — | — | 7.2 | 1.2 | 62 | 91 |

*EG yield = yield of ethylene glycol based on the weight of DTBP added $$\text{TBA + select} = 2 \times \frac{\text{yield of t-butanol obtained (in mmol)}}{\text{wt of DTBP added (in mmol)}} \times 100\%$$

I claim:

1. A process for the production of an alkylene glycol from formaldehyde and either methanol or a secondary alcohol which process comprises reacting the formaldehyde with the methanol or the secondary alcohol in the presence of an organic peroxide having the formula R—O—O—$R^1$ wherein R and $R^1$ are independently either alkyl or aralkyl groups containing from 3 to 12 carbon atoms characterised in that the reaction is carried out in the presence of electromagnetic radiation capable of decomposing the organic peroxide.

2. A process as claimed in claim 1 characterised in that the electromagnetic radiation has a wavelength in range 250 to 400 nanometers.

3. A process as claimed in claim 1 characterised in that the electromagnetic radiation is ultra-violet radiation.

4. A process as claimed in claim 1 characterised in that the secondary alcohol is a monofunctional secondary alcohol.

5. A process as claimed in claim 4 characterised in that the monofunctional secondary alcohol has between 3 and 20 carbon atoms.

6. A process as claimed in claim 5 characterised in that the monofunctional secondary alcohol is selected from the group consisting of propan-2-ol, butan-2-ol, pentan-2-ol, pentan-3-ol, hexan-2-ol, hexan-3-ol, 2-methylpentan-2-ol, 2,3-dimethylbutan-2-ol, cyclohexanol and cycloheptanol.

7. A process as claimed in claim 1 characterised in that ethylene glycol is produced by reaction of formaldehyde with methanol.

8. A process as claimed in claim 1 characterised in that the reactant mixture contains less than 0.5% by weight water.

9. A process as claimed in claim 8 characterised in that the reactant mixture contains less than 0.25% by weight water.

10. A process as claimed in claim 1 characterised in that a polymeric source of formaldehyde is used.

* * * * *

UNITED STATES PATENT AND TRADEMARK OFFICE
CERTIFICATE OF CORRECTION

PATENT NO. : 4,571,289
DATED : February 18, 1986
INVENTOR(S) : Colin George Griggs It is certified that error appears in the above-identified patent and that said Letters Patent is hereby corrected as shown below:

Column 2, line 56, after "hexan-2-ol," insert

-- hexan-3-ol,--.

Column 4, line 22, after "paraformaldehyde", insert

-- $[(CH_2O)_n]$ --.

Signed and Sealed this

Tenth Day of June 1986

[SEAL]

Attest:

DONALD J. QUIGG

Attesting Officer  Commissioner of Patents and Trademarks